United States Patent
Yamashita et al.

(10) Patent No.: US 10,058,617 B2
(45) Date of Patent: Aug. 28, 2018

(54) COMPOSITION FOR FORMING A FILM

(71) Applicant: SHIN-ETSU CHEMICAL CO., LTD, Chiyoda-ku, Tokyo (JP)

(72) Inventors: Tatsuya Yamashita, Joetsu (JP); Takuya Yokosawa, Joetsu (JP); Naosuke Maruyama, Joetsu (JP); Mitsuo Narita, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/376,921

(22) Filed: Dec. 13, 2016

(65) Prior Publication Data

US 2017/0173160 A1 Jun. 22, 2017

(30) Foreign Application Priority Data

Dec. 16, 2015 (JP) ................. 2015-245328

(51) Int. Cl.
*A61K 47/38* (2006.01)
(52) U.S. Cl.
CPC .................... *A61K 47/38* (2013.01)
(58) Field of Classification Search
CPC ....................................... A61K 47/38
USPC ......................................... 514/781
See application file for complete search history.

(56) References Cited

U.S. PATENT DOCUMENTS

| | | | |
|---|---|---|---|
| 3,493,407 | A | 2/1970 | Greminger et al. |
| 3,617,588 | A | 11/1971 | Langman |
| 5,264,223 | A | 11/1993 | Yamamoto et al. |
| 5,431,917 | A | 7/1995 | Yamamoto et al. |
| 6,413,463 | B1 | 7/2002 | Yamamoto et al. |
| 6,649,180 | B1 | 11/2003 | Matsuura et al. |
| 2012/0022169 | A1 | 1/2012 | Moriuchi et al. |
| 2013/0236512 | A1 | 9/2013 | Adden et al. |
| 2014/0088202 | A1 | 3/2014 | Cade et al. |
| 2015/0150817 | A1 | 6/2015 | Hoelzer |

FOREIGN PATENT DOCUMENTS

| | | |
|---|---|---|
| EP | 0401832 A2 | 12/1990 |
| EP | 00714656 A1 | 5/1996 |
| EP | 0714656 A1 | 6/1996 |
| EP | 00401832 A1 | 1/2001 |
| JP | H03009755 A | 1/1991 |
| JP | H08208458 A | 8/1996 |
| JP | 2000136126 A | 5/2000 |
| JP | 2000297102 A | 10/2000 |
| JP | 2001511126 A | 8/2001 |
| JP | 2010270039 A | 12/2010 |
| JP | 2011500871 A | 1/2011 |
| JP | 2013539815 A | 1/2014 |
| JP | 2015522614 A | 8/2015 |
| WO | 2010114134 A2 | 10/2012 |

OTHER PUBLICATIONS

European Search Report and Opinion dated Apr. 13, 2017, and dated Apr. 24, 2017 (11 pages) in European Patent Application No. 16204446.5, filed Dec. 15, 2016, now published as EP 3181126.
Shin-Etsu, Japan Pharmacopoeia, Flydroxypropyl Methyl Cellulose 2910, TC-5, Gastrosoluble Coating Agent and Binder, 2004, pp. 8-9, Shin-Etsu, Japan.
Japanese Notice of Reasons for Refusal 2015-245328 dated Jun. 28, 2018.
Japanese Search Report 2015-245328 dated Jun. 29, 2018.

*Primary Examiner* — Kristin A Vajda
(74) *Attorney, Agent, or Firm* — Williams Mullen; F. Michael Sajovec

(57) ABSTRACT

Provided is a composition for forming a film, the composition not having completely dissolved hydroxypropyl methyl cellulose (HPMC), and enabling formation of the film having a uniform thickness by suppressing the viscosity increase of the composition around an immersion temperature of 50° C. More specifically provided is a composition for forming a film, the composition comprising hypromellose having methoxy group content of 28.0 to 30.0% by weight and hydroxypropoxy group content of 7.6 to 8.5% by weight, wherein a 2% by weight aqueous solution of the hypromellose provides a viscosity at 20° C. of 4.0 to 6.5 mPa·s, a 20% by weight dispersion of the hypromellose provides a viscosity at 50° C. of 2,000 to 11,000 mPa·s, and a 20% by weight aqueous solution of the hypromellose provides a gelation temperature of 54 to 57° C.; and a solvent.

4 Claims, No Drawings

COMPOSITION FOR FORMING A FILM

RELATED APPLICATION

The present application claims priority to Japanese Patent Application No. 2015-245328, filed Dec. 16, 2015, the disclosure of which is incorporated by reference in its entirety.

TITLE OF THE INVENTION

COMPOSITION FOR FORMING A FILM

BACKGROUND OF THE INVENTION

1. Field of the Invention

The present invention relates to a composition for forming a film.

2. Description of the Related Art

Cellulose ethers having low polymerization degrees have been widely applied to pharmaceutical and food fields. Of the cellulose ethers, hypromellose (also known as hydroxypropyl methyl cellulose; hereinafter also called "HPMC") has excellent solubility in water and is dried to form a tough film. The formed film has high transparency and excellent gas barrier and moisture barrier properties, and thus the HPMC is widely applied to the film coating agent for tablets and granules. In addition, the film has excellent film properties, and thus has been used as a pharmaceutical film. As compared with gelatin that has been commonly used as the base material of capsules, the HPMC has no possibility of mad cow disease, is made from plants, and gives high capsule strength even at low water content. Hence, the HPMC is being widely used as the base material of hard capsules.

JP 3-279325A discloses that HPMC, a gelling agent and a gelling adjuvant are dispersed in hot water at 70° C. to obtain a hard capsule preparation liquid containing the HPMC as the base material; then the liquid is adjusted to 50 to 52° C., which is the temperature at which a pin for forming a capsule is immersed (hereinafter also called "immersion temperature"); and a hard capsule having low water content is produced. JP 3-279325A does not disclose a step of cooling the liquid to 35° C. or less before immersion to completely dissolve HPMC. JP 2000-136126A discloses that an HPMC dispersion having the HPMC dispersed in hot water is once cooled to 35° C. or less for completely dissolving the HPMC to obtain a capsule preparation liquid; then the capsule preparation liquid is adjusted to 35 to 50° C., which is lower than the temperature at which HPMC thermally gelates to exhibit rapid viscosity increase of the capsule preparation liquid, so that the viscosity increase of the capsule preparation liquid is suppressed; and uniform hard capsules are produced without strict control of the immersion temperature.

SUMMARY OF THE INVENTION

As for the capsule preparation liquid in which HPMC is not completely dissolved as described in JP 3-279325A, when the temperature of the capsule preparation liquid is slightly changed around 50° C., it is unfortunate that the viscosity rapidly increases (see FIG. 1 in JP 3-279325A). When the viscosity of the capsule preparation liquid becomes higher, the thickness of a capsule shell is difficult to control. Consequently, a hard capsule having a uniform film thickness cannot be obtained so that the engagement between the cap and the body of the capsule deteriorates. To avoid the deterioration of the engagement by strict temperature control of a capsule preparation liquid to a desired high temperature, a complicated apparatus is needed and a complicated control operation is also needed. As for the capsule preparation liquid such as one described in JP 2000-136126A, the step of cooling the capsule preparation liquid to 35° C. or less requires a cooling apparatus. It also takes time for cooling. Thus, the productivity is lowered. Moreover, JP 3-279325A and JP 2000-136126A are silent about the methoxy group content or the hydroxypropoxy group content of the HPMC to be used.

An object of the present invention is to provide a composition for forming a film, the composition having HPMC not completely dissolved, and providing a film having a uniform thickness by suppressing the increase in viscosity of the composition around an immersion temperature of 50° C.

As a result of intensive studies to achieve the object, the present inventors have found a composition for forming a film which can provide the formation of a film having a uniform thickness without reduction of the strength and elongation by using an HPMC dispersion having HPMC not completely dissolved and having a low viscosity at 50° C., and have completed the present invention.

In an embodiment of the present invention, a composition for forming a film, the composition comprising: hypromellose having methoxy group content of 28.0 to 30.0% by weight and hydroxypropoxy group content of 7.6 to 8.5% by weight, wherein a 2% by weight aqueous solution of the hypromellose provides a viscosity at 20° C. of 4.0 to 6.5 mPa·s, a 20% by weight dispersion of the hypromellose provides a viscosity at 50° C. of 2,000 to 11,000 mPa·s, and a 20% by weight aqueous solution of the hypromellose provides a gelation temperature of 54 to 57° C.; and a solvent.

According to the present invention, a film having a uniform thickness can be obtained without reduction of the strength and elongation by using HPMC as a base material while the HPMC is not completely dissolved.

DETAILED DESCRIPTION OF THE PREFERRED EMBODIMENTS

In order to suppress the viscosity increase around the immersion temperature (50° C.) of a composition for forming a film, HPMC capable of providing an HPMC dispersion having a low viscosity can be used. Here, the viscosity of the HPMC dispersion means the viscosity of the dispersion prepared by mixing the HPMC with water while keep the HPMC not completely dissolved. Even when the immersion temperature cannot be strictly controlled, HPMC capable of providing a HPMC dispersion having a low viscosity can suppress the viscosity increase of a composition for forming a film, so that the thickness of a film can be easily controlled to form a uniform film.

The viscosity of an HPMC dispersion commonly depends on the polymerization degree of the HPMC, that is, on the viscosity at 20° C. of a 2% by weight aqueous solution of the HPMC. Thus, in order to lower the viscosity of an HPMC dispersion, HPMC capable of providing a 2% by weight aqueous solution having a low viscosity at 20° C. is thought to be selected. However, as the polymerization degree is reduced, the strength and/or elongation of a resulting film is also reduced.

Accordingly, HPMC which does not lower a viscosity at 20° C. of a 2% by weight aqueous HPMC solution but is capable of providing a HPMC dispersion having a low viscosity at an immersion temperature of 50° C. is used.

A 2% by weight aqueous HPMC solution preferably has a viscosity at 20° C. of 4.0 to 6.5 mPa·s, preferably 4.3 to 6.3 mPa·s, more preferably 4.5 to 6.2 mPa·s.

When the viscosity of the 2% by weight aqueous HPMC solution is less than 4.0 mPa·s, the polymerization degree is excessively low so that the strength and/or elongation of a film is reduced. When the viscosity is more than 6.5 mPa·s, a viscosity of an HPMC dispersion at an immersion temperature increases so that a film having a uniform thickness cannot be obtained.

The 2% by weight aqueous HPMC solution can be prepared by the following procedure. The 6 g of HPMC is weighed and placed in a 500-mL glass beaker, and subjected to addition of hot water of 90° C. to obtain 300 g of a mixture. The mixture is stirred at room temperature for 5 minutes, then stirred at 5° C. for 2 hours or more, and returned to room temperature. As a result, the intended solution can be obtained. When a viscosity at 20° C. of the 2% by weight aqueous HPMC solution is 600 mPa·s or more, it can be determined by using a single cylinder-type rotational viscometer in accordance with "Viscosity measurement by rotational viscometer" in Viscosity Determination of General Tests described in the Japanese Pharmacopoeia 16th Edition. When a viscosity at 20° C. of the 2% by weight aqueous HPMC solution is less than 600 mPa·s, it can be determined by using an Ubbelohde-type viscometer in accordance with "Viscosity measurement by capillary tube viscometer" in Viscosity Determination of General Tests described in the Japanese Pharmacopoeia 16th Edition.

A 20% by weight HPMC dispersion preferably has a viscosity at 50° C. of 2,000 to 11,000 mPa·s, preferably 3,000 to 10,500 mPa·s, more preferably 4,000 to 10,000 mPa·s. When the viscosity at 50° C. of a 20% by weight HPMC dispersion is less than 2,000 mPa·s, a composition containing such HPMC for forming a film to produce a capsule is unlikely to adhere to a capsule formation pin, and thus a resulting capsule shell has a small thickness. When the viscosity is more than 11,000 mPa·s, the film thickness of capsule shell is difficult to control.

A 20% by weight HPMC dispersion of 50° C. can be prepared by the following procedure. The 50 g of HPMC is placed in a 500-mL glass beaker and subjected to addition of hot water of 90° C. to obtain 250 g of a mixture. The mixture is allowed to stand in a warm bath of 80° C. for 10 minutes for degassing, and then stirred at 200 rpm in a warm bath of 60° C. for 30 minutes. While being stirred at 200 rpm, the temperature of the mixture is lowered to 50° C. at a temperature drop rate of 2° C. per 30 minutes. After the temperature thereof has reached 50° C., the mixture is further stirred at the same temperature for 30 minutes. As a result, the intended dispersion can be obtained. The 20% by weight HPMC dispersion of 50° C. thus prepared has HPMC not completely dissolved so that it is in the form of dispersion. The viscosity at 50° C. of the 20% by weight HPMC dispersion can be determined by using a Brookfield viscometer (with a No. 4 rotor at 6 rpm).

HPMC capable of only providing a 2% by weight aqueous solution thereof having a viscosity at 20° C. within the predetermined range and a 20% by weight dispersion thereof having a viscosity at 50° C. within the predetermined range is insufficient. HPMC is required to be capable of not only providing the above but also providing a 20% by weight aqueous solution thereof having a gelation temperature within the predetermined range.

The gelation temperature of 20% by weight aqueous HPMC solution is 54 to 57° C., preferably 55 to 56° C. When the gelation temperature is less than 54° C., the 20% by weight HPMC dispersion is likely to form lumps at 50° C. so that a uniform film cannot be produced. When the gelation temperature is more than 57° C. and no gelling agent is added, the aqueous HPMC solution is required to be heated to 60° C. or higher for gelation. As a result, for example, the composition for forming a film having adhered to the outer surface of a capsule formation pin drips, so that a uniform capsule shell cannot be obtained.

The 20% by weight aqueous HPMC solution can be prepared by the same procedure as that for the 2% by weight aqueous HPMC solution. When many bubbles remain in an aqueous solution, the aqueous solution is, for example, allowed to stand at room temperature overnight for degassing. The gelation temperature of the prepared 20% by weight aqueous HPMC solution can be determined by using, for example, MCR301, which is a rheometer manufactured by Anton Paar. The 20% by weight aqueous HPMC solution is placed at a sample measurement part of the rheometer, which has been adjusted to 20° C. Parallel plates (PP-50) having a diameter of 50 mm φ are used as the measurement jigs, and the measurement gap is set at 0.5 mm. The outer periphery of the measurement jigs is covered with silicone oil, and the sample is allowed to stand at 20° C. for 5 minutes and then subjected to a distortion with a frequency of 1 Hz and amplitude of 1% to start the measurement. The temperature of the sample measurement part is increased to 90° C. at a increase rate of 2° C. per minute with a Peltier temperature controller. The data are collected at two points per minute.

The storage elastic modulus G'(20→90° C.) obtained by the measurement typically represents the elastic properties of a solution, and the loss elastic modulus G"(20→90° C.) typically represents the viscosity properties of a solution. In other words, a measurement sample in a liquid state shows G">G', and a measurement sample in a gel (solid) state shows G"<G'. Hence, the temperature at which G" is equal to G' is regarded as the gelation temperature.

As for the methoxy group content and the hydroxypropoxy group content of the HPMC, the methoxy group content is 28.0 to 30.0% by weight, preferably 28.5 to 29.5%, and the hydroxypropoxy group content is 7.6 to 8.5% by weight, preferably 7.7 to 8.4%, more preferably 7.9 to 8.3%, from the standpoint of the viscosity at 50° C. of a 20% by weight HPMC dispersion and the gelation temperature of a 20% by weight aqueous HPMC solution. The hydroxypropoxy group has a hydroxy group as a hydrophilic group so that the content thereof affects the solubility in water at 50° C. or higher, or affects the viscosity at 50° C. of a 20% by weight HPMC dispersion.

The methoxy group content and the hydroxypropoxy group content of HPMC can be determined by an analytical method described in the Japanese Pharmacopoeia 16th Edition.

The composition for forming a film comprises a solvent in addition to the HPMC. The solvent may be of any type as long as it can dissolve the HPMC, and is preferably, for example, water or a mixed solvent of water and an alcohol such as ethanol and methanol. From the standpoint of safety and environmental aspects, the solvent is particularly preferably purified water. From the standpoint of control of the film thickness, the solvent may be comprised in such an amount that the HPMC content is 15 to 25% by weight in the composition for forming a film.

The composition for forming a film may comprise an optional gelling agent. The gelling agent may be any agent capable of making the composition for forming a film into a gel in a step of cooling the composition from an immersion temperature to room temperature (15 to 35° C.). Examples of the gelling agent include carrageenans such as κ-carrageenan and t-carrageenan, pectin, agar, gelatin and gellan gum. Of them, a carrageenan is preferably used because of excellent gel strength.

In the composition for forming a film, the content of the gelling agent is preferably 0.1 to 0.5% by weight. When the content of the gelling agent is less than 0.1% by weight, the gelation may be insufficient. When the content is more than 0.5% by weight, the viscosity of the composition for forming a film may increase around the immersion temperature (50° C.).

In the absence of the gelling agent, the gelation of the HPMC is utilized. Thus, the composition for forming a film is preferably heated to a temperature equal to or higher than the immersion temperature, for example, heated to 60° C. or higher, so as to become gelated. In the absence of the gelling agent, the viscosity at 20° C. of a 2% by weight aqueous solution is preferably as high as possible in order to prevent the composition for forming a film from dripping.

The composition for forming a film may further comprise a gelling adjuvant to help the gelling agent to function sufficiently. The gelling adjuvant is appropriately selected according to a type of the gelling agent. For example, when the gelling agent is κ-carrageenan, a potassium salt such as potassium chloride may be selected. When the gelling agent is t-carrageenan, a calcium salt such as calcium chloride may be selected.

In the composition for forming a film, the content of the gelling adjuvant is preferably 0.01 to 0.5% by weight. When the content of the gelling adjuvant is less than 0.01% by weight, the gelling adjuvant may function insufficiently. When the content is more than 0.5% by weight, the viscosity of the dispersion may increase around the immersion temperature (50° C.) of the composition.

The composition for forming a film may be prepared by mixing the above HPMC, the solvent, and the optional gelling agent with or without the gelling adjuvant. The mixing temperature is preferably higher than the immersion temperature (preferably 40 to 60° C., more preferably 50° C.) at which a film formation plate or pin or the like is immersed, but preferably not higher than 95° C. The mixing temperature is more preferably 65 to 95° C. After the mixing, the mixture is particularly preferably cooled to the immersion temperature of a film formation plate or pin or the like so that a composition for forming a film is obtained at the immersion temperature. This procedure is preferred because when the mixing temperature is higher than the immersion temperature and then the resulting mixture is cooled to the immersion temperature, the HPMC is not completely dissolved and the viscosity at 50° C. of the 20% by weight HPMC dispersion is allowed to be within the predetermined range, in the absence of excess cooling. The composition for forming a film is in the form of dispersion at the immersion temperature since the HPMC is not completely dissolved.

A film can be formed by the following procedure. A film formation substrate such as a food, a tablet, a film formation plate (e.g. a glass plate or a metal plate) and a capsule formation pin is immersed in the composition for forming a film at an immersion temperature, and then taken out to allow the composition to adhere to the periphery of the film formation substrate, thereby forming a film. In the present application, the immersion includes coating, and a film can be formed by coating a film formation plate by using a bar coater or a film applicator at an immersion temperature (coating temperature). The formed film can be dried, and then separated by peeling from the film formation plate.

Next, a preferred example of the method for producing the HPMC will be described. The HPMC can be produced by the method comprising the steps of: bringing cellulose into contact with an alkali metal hydroxide solution to obtain alkali cellulose, subjecting the alkali cellulose to etherification reaction to obtain HPMC, and subjecting the HPMC to depolymerization reaction with an acid to obtain an intended HPMC which can provide the reduced viscosity at 20° C. of a 2% by weight aqueous solution.

Examples of the method of producing alkali cellulose include a method comprising a step of spraying or adding dropwise an alkali metal hydroxide solution to a powdery pulp under stirring, and a method comprising the steps of immersing a pulp sheet in an excess amount of an alkali metal hydroxide solution to allow the pulp sheet to sufficiently absorb the alkali metal hydroxide solution, and pressing the pulp sheet for removal of an excess alkali metal hydroxide to leave an intended amount of alkali metal hydroxide behind.

The alkali metal hydroxide solution to be used may be any solution as long as it can produce alkali cellulose, and sodium hydroxide is preferred from the standpoint of economy. The concentration of the alkali metal hydroxide solution is preferably 23 to 60% by weight from the standpoint of the contents of ether substituents, economy and operability. The concentration of the alkali metal hydroxide solution to be brought into contact with pulp is preferably kept constant to stabilize the composition of alkali cellulose and keep the transparency of HPMC to be produced.

The weight ratio of the alkali metal hydroxide to the cellulose component (alkali metal hydroxide/cellulose component) contained by the obtained alkali cellulose is not particularly limited as long as intended methoxy group and hydroxypropoxy group contents will be produced. The weight ratio is preferably 0.3 to 1.5 from the standpoint of the quality of HPMC to be produced.

Thereafter, the alkali cellulose is reacted with an etherifying agent in a usual manner for the etherification reaction of the alkali cellulose. Examples of the etherifying agent include methyl chloride and propylene oxide. The weight ratio of methyl chloride to sodium hydroxide in the alkali cellulose (methyl chloride/sodium hydroxide) or the weight ratio of propylene oxide to the cellulose component (propylene oxide/cellulose component) is not particularly limited as long as intended methoxy group and hydroxypropoxy group contents are obtained. From the standpoint of controllability of the methoxy group and hydroxypropoxy group contents and economy, methyl chloride is preferably used in such an amount as to give a weight ratio of the methyl chloride to the sodium hydroxide (methyl chloride/sodium hydroxide) of 0.9 to 1.6. Similarly, propylene oxide is preferably used in such an amount as to give a weight ratio of the propylene oxide to the cellulose component (propylene oxide/cellulose component) of 0.32 to 0.46.

The reaction product of the alkali cellulose with an etherifying agent is washed and then dried to obtain HPMC. Examples of the typical washing include washing with water (preferably hot water of 60 to 100° C.) and washing with an organic solvent or a mixed solvent of an organic solvent and water. For example, the reaction product is sent to a washer and filtered to yield a cake, and then the cake is subjected to spraying of hot water, filtered again and washed.

The washed reaction product is optionally pressed or squeezed. The press or squeeze can be carried out preferably by using a continuous press or squeezer. The pressing or squeezing mechanism by the continuous press or squeezer is not particularly limited as long as a cake can be continuously pressed or squeezed.

The washed and optionally pressed or squeezed reaction product is dried. The drying may be carried out by, for example, a hot air system, a conduction heating system, or a combination thereof.

The dried HPMC is subjected to optional pulverization. The pulverization method is not particularly limited. Examples of the pulverization method include a method of using an impact grinder in which a product is ground through collision of each other or through collision with a collision substrate, and a method of using a ball mill, a roller mill or the like in which a product is ground by pinching the product between substrates.

The optionally pulverized HPMC having a high polymerization degree can be subjected to depolymerization reaction to obtain HPMC having a low polymerization degree and having a predetermined viscosity of a 2% by weight aqueous solution.

Examples of the depolymerization reaction include depolymerization by hydrolysis in the presence of an acid catalyst, and depolymerization by oxidative decomposition in the presence of an oxidizing agent. The depolymerization is preferably depolymerization by hydrolysis in the presence of an acid catalyst.

The acid to be used for the depolymerization by hydrolysis in the presence of an acid catalyst may be in a gas state, a liquid state or a solution state and be of any type as long as an aqueous solution thereof provides protons. Typically, hydrogen chloride gas, an aqueous hydrochloric acid solution, or an alcohol solution of hydrogen chloride is used. Examples of the acid preferably include inorganic acids such as hydrochloric acid, sulfuric acid, nitric acid and phosphoric acid, which can be used alone or as a mixture of two or more. Hydrochloric acid is preferred from the standpoint of the safety of a salt to be produced by neutralization of the acid. The concentration of hydrochloric acid is preferably 1 to 45% by weight.

For example, when hydrogen chloride is selected as the acid catalyst, the amount of the acid catalyst to be added is preferably 0.04 to 1 part by weight relative to 100 parts by weight of the starting HPMC from the standpoint of the reaction controllabilty.

When an acid catalyst is used, the reaction temperature is preferably 40 to 85° C. and the reaction time is preferably 0.1 to 4 hours from the standpoint of appropriate control the reaction rate.

EXAMPLES

The present invention will next be described in further detail with reference to Examples and Comparative Examples. It should not be construed that the invention is limited to or by Examples.

Example 1

Wood pulp chips having a polymerization degree of 2,100 were immersed in a 49% by weight aqueous sodium hydroxide solution, and then subjected to removal of excess sodium hydroxide to produce alkali cellulose having a weight ratio of alkali metal hydroxide to the cellulose component in the alkali cellulose of 1.25, wherein the weight ratio was determined by a titration method. The obtained alkali cellulose was placed in a 100-L pressure-resistant reactor in such an amount as to give 5.5 kg of a cellulose component. After vacuuming, 11.7 kg of methyl chloride and 2.15 kg of propylene oxide were added thereto and reacted, while increasing the reactor temperature from 60° C. to 80° C. The crude reaction product was washed with hot water, and dried in a dryer using both jacket heating and hot air heating until a drying loss reached 2% by weight. The dried product was then subjected to impact grinding to yield HPMC. A viscosity at 20° C. of a 2% by weight aqueous solution of the HPMC was 4,000 mPa·s, when the viscosity was determined by the measurement method in accordance with the Japanese Pharmacopoeia.

The 1 kg of the obtained HPMC was placed in a 20 L Henschel mixer, and subjected to spraying of 12% by weight hydrochloric acid while mixed with stirring at 200 rpm. The spraying amount was controlled in such way as to give an HCl amount of 0.3% by weight relative to the HPMC. The 500 g of the resulting mixture was transferred into a 2-L glass reactor for depolymerization reaction of 60 minutes with the glass reactor rotated in a water bath of 80° C.

The contents of substituents, the viscosity, and the gelation temperature of the obtained HPMC are shown in Table 1. The obtained HPMC was used to produce a film in the following procedure, and the strength and the elongation of the film were measured. The results are shown in Table 1.

<Tensile Test>

The 30 to 40 g of a 20% by weight aqueous HPMC solution was dropped onto a horizontal glass plate, and was quickly drawn with a YBA type Baker applicator (manufactured by Yoshimitsu Seiki) having a coating clearance of 750 to 850 μm. The coating was dried at 60° C. until the water content thereof reached 5% by weight or less, while keeping the glass plate horizontally. A film was peeled off from the glass plate to obtain the film having a thickness of 100±5 μm. The obtained film was cut into pieces, each piece having a width of 1 cm and a length of 8 cm. Ten film pieces were dried at 105° C. for 2 hours and subjected to humidity control at 52% RH and 25° C. for 3 days to have water content of 5 to 8% by weight. As a result, test film pieces were prepared.

The tensile test was carried out by using a Tensilon universal tester (RTC-1310A, manufactured by Orientec Co., Ltd.), and the strength and the elongation of film pieces were measured. Each test film piece was clamped with upper and lower jaws at a position 2 cm apart from each end of the test film piece, and the tensile measurement was carried out in conditions of a span of 4 cm, a test speed of 10 mm/min, a load range of 10% RO, and a load cell rating of 10 kgN, at 50 to 60% RH and 25° C. The averages (n=10) of the strength and the elongation at the time of film breakage were calculated.

<Preparation of Composition for Forming a Film and Evaluation of Thickness Uniformity of Film Obtained>

The 50 g of HPMC (20% by weight), 0.50 g of κ-carrageenan (0.2% by weight, manufactured by Tokyo Chemical Industry Co., Ltd.) and 0.25 g of potassium chloride (0.1% by weight, manufactured by Wako Pure Chemical Industries, Ltd.) were placed in a 500-mL glass beaker, and subjected to addition of hot water of 90° C. to obtain 250 g of a mixture. The mixture was allowed to stand in a warm bath of 80° C. for 10 minutes for degassing. Next, the mixture was stirred at 200 rpm in a warm bath of 60° C. for 30 minutes, and then cooled to an immersion temperature of 50° C. at a decrease rate of 2° C. per 30 minutes while keeping the mixture stirred at 200 rpm. After the mixture reached 50° C., the mixture was further stirred at 50° C. for 30 minutes to obtain a composition for forming a film.

The 10 g of the composition of 50° C. was dropped onto a horizontal glass plate at room temperature, and quickly drawn with a YBA type Baker applicator (manufactured by Yoshimitsu Seiki) having a coating clearance of 900 µm. The glass plate was vertically placed in such a way as to make the direction to which the composition was drawn (hereinafter also called "lower end" direction) become the downward direction, to dry the coating at room temperature until the water content reached 10% by weight or less. Then the film was peeled off from the glass plate to obtain the film containing a gelling agent.

A position 2 cm apart from the lower end in the length direction of the obtained film was regarded as the starting point, and the film thickness was determined at a total of 10 points which were positioned at an interval of 1 cm in the length direction from the starting point. The results of the average, the maximum, and the minimum of the film thickness are shown in Table 1.

Example 2

HPMC was produced in the same manner as in Example 1 except that the amount of propylene oxide was changed to 2.37 kg. The produced HPMC was subjected to evaluation of the strength, the elongation, and the film thickness uniformity in the same manner as in Example 1. The results are shown in Table 1.

Example 3

HPMC was produced in the same manner as in Example 1 except that the depolymerization reaction was carried out for 75 minutes with the depolymerization reactor rotated in a water bath of 81° C. The produced HPMC was subjected to evaluation of the strength, the elongation, and the film thickness uniformity in the same manner as in Example 1. The results are shown in Table 1.

Example 4

HPMC was produced in the same manner as in Example 1 except that the depolymerization reaction was carried out for 90 minutes with the depolymerization reactor rotated in a water bath of 82° C. The produced HPMC was subjected to evaluation of the strength, the elongation, and the film thickness uniformity in the same manner as in Example 1. The results are shown in Table 1.

Comparative Example 1

HPMC was produced in the same manner as in Example 1 except that 2.7 kg of propylene oxide was added and reacted. The produced HPMC was subjected to evaluation of the strength, the elongation, and the film thickness uniformity in the same manner as in Example 1. The results are shown in Table 1.

Comparative Example 2

HPMC was produced in the same manner as in Example 1 except that 1.78 kg of propylene oxide was added and reacted. The produced HPMC was subjected to evaluation of the strength, the elongation, and the film thickness uniformity in the same manner as in Example 1. The results are shown in Table 1.

Comparative Example 3

HPMC was produced in the same manner as in Example 1 except that the weight ratio of alkali metal hydroxide to the cellulose component in the alkali cellulose was changed to 1.24, the amount of methyl chloride was changed to 11.2 kg, and the amount of propylene oxide was changed to 1.54 kg. The produced HPMC was subjected to evaluation of the strength, the elongation, and the film thickness uniformity in the same manner as in Example 1. The results are shown in Table 1.

Comparative Example 4

HPMC was produced in the same manner as in Example 1 except that the depolymerization reaction was carried out for 120 minutes with the depolymerization reactor rotated in a water bath of 84° C. The produced HPMC was subjected to evaluation of the strength, the elongation, and the film thickness uniformity in the same manner as in Example 1. The results are shown in Table 1.

TABLE 1

| | substituent content | | viscosity | | gellation temp. | tensile test | | thickness | | | |
|---|---|---|---|---|---|---|---|---|---|---|---|
| | methoxy | hydroxy-propoxy | at 20° C. of 2 wt % | at 50° C. 20 wt % | 20→90° C. 20 wt % | | | | | | difference between |
| | group (wt %) | group (wt %) | aq. solution (mPa · s) | dispersion (mPa · s) | aq. solution (° C.) | strength (kg/cm$^2$) | elongation (%) | average (µm) | maximum (µm) | minimum (µm) | max. and min. (µm) |
| Example 1 | 29.0 | 8.1 | 6.0 | 9,200 | 56 | 523 | 16.5 | 102 | 106 | 99 | 7 |
| Example 2 | 29.2 | 8.4 | 6.1 | 10,000 | 57 | 518 | 16.8 | 103 | 107 | 100 | 7 |
| Example 3 | 29.0 | 8.0 | 5.3 | 6,700 | 56 | 510 | 15.0 | 101 | 105 | 99 | 6 |
| Example 4 | 29.0 | 8.0 | 4.5 | 3,500 | 55 | 502 | 13.3 | 99 | 102 | 96 | 6 |
| Comp. Ex. 1 | 29.1 | 9.1 | 6.0 | 13,100 | 58 | 515 | 17.4 | 111 | 115 | 105 | 10 |
| Comp. Ex. 2 | 29.2 | 7.0 | 6.1 | 4,400 | 52 | 519 | 15.5 | 100 | 107 | 96 | 11 |
| Comp. Ex. 3 | 29.3 | 6.0 | 6.2 | 3,300 | 50 | 536 | 14.8 | 98 | 105 | 94 | 11 |
| Comp. Ex. 4 | 29.0 | 8.0 | 3.2 | 2,600 | 54 | 426 | 5.6 | 96 | 98 | 92 | 6 |

It was found that the films of Examples 1 to 4 had smaller differences between the maximum thickness and the minimum thickness than those of the films of Comparative Examples 1 to 3, and thus had higher film uniformity.

In Comparative Example 1, the 20% by weight HPMC dispersion had a high viscosity at 50° C. so that sufficient flowability was not achieved and a uniform film thickness was not achieved. Such a composition for forming a film is difficult to use for capsules which are considered preferably to have a difference between the maximum film thickness and the minimum film thickness of less than 10 μm from the standpoint of engagement of the cap and the body of a capsule.

In Comparative Example 2 or 3, the hydroxypropoxy group content was low so that the 20% by weight aqueous HPMC solution had a low gelation temperature. The composition for forming a film contained many lumps at 50° C. so that a uniform film thickness was not achieved. Hence, the composition is difficult to use for capsules because of the same reason as in Example 1.

The film of Comparative Example 4 had thickness uniformity almost equal to those of Examples 1 to 4, but the HPMC had a low polymerization degree so that the 2% by weight aqueous HPMC solution had a low viscosity at 20° C. Thus, the strength and the elongation of the film were inferior to those of Examples 1 to 4.

The invention claimed is:

1. A composition for forming a film, the composition comprising:
   hypromellose having methoxy group content of 28.0 to 30.0% by weight and hydroxypropoxy group content of 7.6 to 8.5% by weight, wherein a 2% by weight aqueous solution of the hypromellose provides a viscosity at 20° C. of 4.0 to 6.5 mPa·s, a 20% by weight dispersion of the hypromellose provides a viscosity at 50° C. of 2,000 to 11,000 mPa·s, and a 20% by weight aqueous solution of the hypromellose provides a gelation temperature of 54 to 57° C.; and
   a solvent.

2. The composition according to claim 1, further comprising a gelling agent.

3. The composition according to claim 1, further comprising a gelling adjuvant.

4. The composition according to claim 2, further comprising a gelling adjuvant.

* * * * *